United States Patent
Buck et al.

(10) Patent No.: US 11,672,979 B2
(45) Date of Patent: Jun. 13, 2023

(54) DEVICE TO INDUCE ELECTRICAL MUSCLE RELAXATION FOR AIRWAY MANAGEMENT

(71) Applicants: David Buck, Cincinnati, OH (US); Mor Mordechai Peretz, Lehavim (IL)

(72) Inventors: David Buck, Cincinnati, OH (US); Mor Mordechai Peretz, Lehavim (IL)

( * ) Notice: Subject to any disclaimer, the term of this patent is extended or adjusted under 35 U.S.C. 154(b) by 1133 days.

(21) Appl. No.: 16/211,192

(22) Filed: Dec. 5, 2018

(65) Prior Publication Data

US 2019/0167984 A1 Jun. 6, 2019

Related U.S. Application Data

(60) Provisional application No. 62/595,018, filed on Dec. 5, 2017.

(51) Int. Cl.
| | | |
|---|---|---|
| *A61N 1/36* | (2006.01) | |
| *H02M 3/158* | (2006.01) | |
| *H02M 1/08* | (2006.01) | |
| *H02M 3/157* | (2006.01) | |
| *A61N 1/04* | (2006.01) | |

(Continued)

(52) U.S. Cl.
CPC ....... *A61N 1/3601* (2013.01); *A61M 16/0488* (2013.01); *A61N 1/0452* (2013.01); *A61N 1/36034* (2017.08); *H02M 1/08* (2013.01); *H02M 3/157* (2013.01); *H02M 3/158* (2013.01); *A61M 2205/054* (2013.01);

(Continued)

(58) Field of Classification Search
CPC .............. A61M 16/04; A61M 16/0488; A61M 2205/054; A61N 1/3601; A61N 1/36043; A61N 1/0452; H02M 3/157; H02M 3/158
See application file for complete search history.

(56) References Cited

U.S. PATENT DOCUMENTS

| | | | | |
|---|---|---|---|---|
| 4,372,319 A | * | 2/1983 | Ichinomiya .......... | A61N 1/3603 607/63 |
| 4,387,723 A | * | 6/1983 | Atlee, III ............. | A61B 5/1106 600/595 |

(Continued)

OTHER PUBLICATIONS

Williamson and Andrews, Localized Electrical Nerve Blocking, Mar. 2005, IEEE Transactions on Biomedical Engineering, vol. 52, No. 3, pp. 363-370 (Year: 2005).*

(Continued)

*Primary Examiner* — Carl H Layno
*Assistant Examiner* — Manolis Pahakis
(74) *Attorney, Agent, or Firm* — Bose McKinney & Evans LLP

(57) ABSTRACT

A system to induce electrical muscle relaxation for airway management. The illustrative system includes a power control system targeted to relax muscles associated with an airway channel, and more particularly, to assist in human intubation by placement of an endotracheal tube within the trachea of a patient, mask ventilation, and/or resolution of laryngospasm. The relaxation of the muscles is achieved through external stimulation of nerves through the skin by an output electrical current pattern applied by the power control system. The illustrative system is configured to independently regulate an output current frequency and an output current amplitude of the output electrical current pattern.

12 Claims, 10 Drawing Sheets

(51) Int. Cl.
  *A61M 16/04* (2006.01)
  *H02M 1/00* (2006.01)
  *H02M 7/48* (2007.01)
(52) U.S. Cl.
  CPC .......... *H02M 1/007* (2021.05); *H02M 1/0009* (2021.05); *H02M 7/4815* (2021.05)

(56) References Cited

U.S. PATENT DOCUMENTS

| | | | | |
|---|---|---|---|---|
| 4,446,870 | A * | 5/1984 | Wing | A61N 1/32 128/907 |
| 4,535,777 | A * | 8/1985 | Castel | A61N 1/36021 607/71 |
| 4,907,602 | A * | 3/1990 | Sanders | A61N 1/3601 607/72 |
| 4,960,124 | A * | 10/1990 | Masaki | A61N 1/32 607/70 |
| 5,658,322 | A * | 8/1997 | Fleming | A61N 1/40 607/66 |
| 5,792,067 | A * | 8/1998 | Karell | A61N 1/36031 607/42 |
| 5,857,957 | A * | 1/1999 | Lin | A61N 2/02 600/13 |
| 5,995,872 | A | 11/1999 | Bourgeois | |
| 6,208,896 | B1 * | 3/2001 | Mulhauser | A61N 1/3956 607/5 |
| 6,269,269 | B1 * | 7/2001 | Ottenhoff | A61N 1/3601 607/42 |
| 7,583,991 | B2 | 9/2009 | Rea | |
| 8,290,582 | B2 * | 10/2012 | Lin | A61B 18/14 606/41 |
| 8,844,537 | B1 * | 9/2014 | Abramson | A61B 5/4836 607/42 |
| 9,364,667 | B1 * | 6/2016 | Dinsmoor | A61N 1/36007 |
| 10,058,669 | B2 | 8/2018 | Razavi et al. | |
| 2001/0018547 | A1 * | 8/2001 | Mechlenburg | A61N 2/006 600/15 |
| 2003/0199945 | A1 * | 10/2003 | Ciulla | A61N 1/36003 607/48 |
| 2005/0267547 | A1 * | 12/2005 | Knudson | A61N 1/36017 607/48 |
| 2007/0106338 | A1 * | 5/2007 | Errico | A61N 1/3611 607/42 |
| 2007/0150006 | A1 * | 6/2007 | Libbus | A61N 1/36185 607/2 |
| 2007/0156182 | A1 * | 7/2007 | Castel | A61N 1/36034 607/2 |
| 2007/0191902 | A1 * | 8/2007 | Errico | A61N 1/0551 607/42 |
| 2007/0213782 | A1 * | 9/2007 | Shaw | A61N 1/3601 607/42 |
| 2007/0239210 | A1 * | 10/2007 | Libbus | A61N 1/36114 607/2 |
| 2008/0183248 | A1 * | 7/2008 | Rezai | A61N 1/0553 607/116 |
| 2008/0243196 | A1 * | 10/2008 | Libbus | A61N 1/0551 607/2 |
| 2008/0275525 | A1 * | 11/2008 | Stone | A61N 1/3601 607/42 |
| 2009/0024186 | A1 * | 1/2009 | Brockway | A61N 1/36114 607/59 |
| 2009/0036945 | A1 * | 2/2009 | Chancellor | A61N 1/36175 607/39 |
| 2009/0076561 | A1 * | 3/2009 | Libbus | A61N 1/36117 607/11 |
| 2009/0155336 | A1 * | 6/2009 | Rezai | A61P 9/10 424/423 |
| 2009/0240199 | A1 * | 9/2009 | Rahimsobhani | A61M 16/0459 604/101.02 |
| 2009/0312817 | A1 * | 12/2009 | Hogle | A61B 5/682 607/54 |
| 2010/0114510 | A1 * | 5/2010 | Vaingast | G01R 31/3648 702/62 |
| 2010/0174341 | A1 * | 7/2010 | Bolea | A61B 5/4818 607/42 |
| 2010/0241188 | A1 * | 9/2010 | Errico | A61N 1/3601 607/42 |
| 2010/0298905 | A1 * | 11/2010 | Simon | A61N 1/0456 607/66 |
| 2011/0093032 | A1 * | 4/2011 | Boggs, II | A61N 1/3611 607/42 |
| 2011/0230702 | A1 * | 9/2011 | Honour | A61N 1/36017 607/42 |
| 2011/0319958 | A1 * | 12/2011 | Simon | A61N 2/006 607/42 |
| 2012/0184801 | A1 * | 7/2012 | Simon | A61N 1/36025 607/45 |
| 2012/0253249 | A1 * | 10/2012 | Wilson | A61N 1/3611 607/42 |
| 2013/0090712 | A1 * | 4/2013 | Popovic | A61N 1/0476 607/148 |
| 2013/0197321 | A1 * | 8/2013 | Wilson | A61B 7/008 607/42 |
| 2013/0204314 | A1 * | 8/2013 | Miller, III | A61B 5/6867 607/42 |
| 2013/0238049 | A1 * | 9/2013 | Simon | A61N 1/36034 607/42 |
| 2013/0245722 | A1 * | 9/2013 | Ternes | A61N 1/372 607/62 |
| 2014/0067021 | A1 * | 3/2014 | Rezai | A61N 1/36078 607/115 |
| 2014/0276270 | A1 * | 9/2014 | Ludlow | A61N 5/0622 601/46 |
| 2014/0324118 | A1 * | 10/2014 | Simon | A61B 5/7267 607/46 |
| 2015/0073232 | A1 * | 3/2015 | Ahmad | A61B 5/11 607/42 |
| 2015/0112416 | A1 * | 4/2015 | Mashiach | A61N 1/3611 607/134 |
| 2015/0174397 | A1 * | 6/2015 | Bhadra | A61N 1/06 607/117 |
| 2015/0209583 | A1 * | 7/2015 | Pitts | A61B 5/4205 607/48 |
| 2016/0045739 | A1 * | 2/2016 | Rezai | A61N 1/36096 607/45 |
| 2016/0150993 | A1 * | 6/2016 | Powell | A61B 5/296 600/301 |
| 2017/0196513 | A1 * | 7/2017 | Longinotti-Buitoni | A61B 5/7405 |
| 2017/0196761 | A1 * | 7/2017 | Hyde | A61M 16/0069 |
| 2017/0197075 | A1 * | 7/2017 | Van Bruggen | A61N 1/3611 |
| 2017/0197081 | A1 * | 7/2017 | Charlesworth | A61N 1/36034 |
| 2019/0351227 | A1 * | 11/2019 | Feskov | A61N 1/3603 |
| 2020/0139138 | A1 * | 5/2020 | Sit | A61N 1/378 |

OTHER PUBLICATIONS

Ackermann, Jr., PhD, Christian Ethier, PhD, Emily L. Foldes, MS, Emily R. Oby, Dustin Tyler, PhD, Matt Bauman, Nilroy Bhadra, MD, PhD, Lee Miller, PhD, and Kevin L. Kilgore, PhD, Electrical Conduction Block in Large Nerves: High-Frequency Current Delivery in the Nonhuman Primate, Muscle & Nerve, Jun. 2011, 3 pages.

Narendra Bhadra, Niloy Bhadra, Kevin Kilgore and Kenneth J. Gustafson, High Frequency Electrical Conduction Block of the Pudendal Nerve, J. Neural Eng. 3 (2006) 180-187, 14 pages.

Ira Sanders, MD, Jonathan Aviv, MD, Michael M. Racenstein, Warren M. Kraus and Hugh F. Biller, MD, Transcutaneous Electrical Stimulation of the Recurrent Laryngeal Nerve in Monkeys, Ann Otol Rhinol Laryngeal 96:1987, 5 pages.

Jonathan J. Waataja, Katherine S. Tweden and Christopher N. Honda, Effects of High-Frequency Alternating Current on Axonal Conduction Through the Vagus Nerve, IOP Publishing Ltd, Printed in the Uk, J. Neural Eng. 8 (2011) 056013, 7 pages.

K. L. Kilgore and N. Bhadra, Nerve Conduction Block Utilising High-Frequency Alternating Current, Medical & Biological Engineering & Computing 2004, vol. 42, 14 pages.

(56) References Cited

OTHER PUBLICATIONS

Anirudhan Narasimhan, Commercialization of HFAC Electronic Nerve Block Technology to Treat Chronic Post Surgical Pain, Department of Biology, Case Western Reserve University, Jan. 2011, 57 pages.
Yong-Ann Ang, David Stone, Chris Bingham, Martin Foster, Rapid Analysis & Design Methodologies of High-Frequency LCLC Resonant Inverter as Electrodeless Fluorescent Lamp Ballast, Copyright 2007, 6 pages.
Microchip, 16-Bit Digital Signal Controllers with High-Speed PWM, ADC and Comparators, Copyright 2009-2012, Microchip Technology, Inc., 456 pages.
Yogi A. Patel and Robert J. Butera, Differential Fiber-Specific Block of Nerve Conduction in Mammalian Pheripheral Nerves Using Kilohertz Electrical Stimulation, J. Neurophysiol 113: 3923-3929, 2015, First published Apr. 15, 2015; doi:10.1152/jn.00529.2014, 7 pages.
Narendra Bhadra, Emily Foldes, Tina Vrabec, Kevin Kilgore and Nilroy Bhadra, Temporary persistence of conduction block after prolonged Kilohertz frequency alternating current on rat sciatic nerve, J. Neural Eng. 15 (2018) 016012 (9pp), 9 pages.
Hassan Pooya Forghani-zadeh and Gabriel A. Rincon-Mora, Current-Sensing Techniques for DC-DC-Converters, 2002, 4 pages.
Kevin L. Kilgore and Niloy Bhadra, Reversible Nerve Conduction Block Using Kilohertz Frequency Alternating Current, Copyright 2013 International Neuromodulation Society, Neuromodulation 2014; 17: 242-255, 14 pages.
R. L. Steigerwald, A Comparison of Half-Bridge Resonant Converter Topologies, General Electric Company, 1987, 10 pages.
Mi-Na Kim, Yong-Su Noh, Jun-Gu Kim, Tae-Won Lee, Chung-Yuen Won, A New Active Power Decoupling using Bi-directional Resonant Converter for Flyback-type AC-module system, 2012 IEEE Vehicle Power and Propulsion Conference, Oct. 9-12, 2012, Seoul, Korea, 5 pages.
J. M. Correa, E. D. Hutto, F. A. Farret and M. Godoy Simoes, A Fuzzy-Controlled Pulse Density Modulation Strategy for a Series Resonant Inverter with Wide Load Range, 2003, 6 pages.
F. J. Ferrero, M. Rico, J. M. Alonso, M. Gonzalez and J.C. Campo, A Unity Power Factor Electronic Ballast for HPS Lamps, Resonant Current Controlled, 1998, 8 pages.
Michael Evzelman, Hongjie Wang, Regan Zane and Xiaoliang Zhao, Two-Stage Sinusoidal Generator with Calibration and Pulse Train Amplitude Feedback for Ultrasonic Applications, 2017, 7 pages.
Guan-Chyun Hsieh and Chien-Ming Wang, One-Cycle Controlled Half-Bridge Series-Resonant DC to AC Inverter with Reduced Conduction Loss, Department of Electronic Engineering, National Taiwan University of Science and Technology, 2002, 6 pages.
Sam Ben-Yaakov, Mor Mordechai Peretz, Jorge M. Parra Sr. and Jorge M. Parra Jr., Self-Oscillating Constant-Current Fluorescent Lamp Driver: Theory and Application, Power Electronics Laboratory, Department of Electrical and Computer Engineering, Ben-Gurion University of the Negev, 2007, 7 pages.

Daniel Jolley, If sugammadex is the answer what is the question? Gas Exchange. Retrieved Jan. 7, 2016 from http://gasexchange.com/articles/sugammadex-is-the-answer-what-is-the-question, 12 pages.
B. Dobrucky, M. Prazenica, S. Kascak and J. Kassa, HF Link LCTLC Resonant Converter with LF AC Output, Faculty of Electrical Engineering, University of Zilina, 2012, 6 pages.
Ronald D. Miller, MD, Sugammadex: An Opportunity to Change the Practice of Anesthesiology?, vol. 104, No. 3, Mar. 2007, 2 pages.
Hao Leo Li, Aiguo Hu and Grant A. Covic, Development of a Discrete Energy Injection Inverter for Contactless Power Transfer, The University of Auckland, 2008, 5 pages.
J.L. Apfelbaum, C.A. Hagberg, R.A. Caplan, C.D. Blitt, R.T. Conis and Nickinovich, D.G. Practice guidelines for management of the difficult airway: an updated report by the American society of anesthesiologists' task force on management of the difficult airway. Anesthesiology, 2013; 118:251-270, 20 pages.
Georgia Kostopanagiotou, Vassilios Smyrniotis, MD, PhD, Nikolaos Arkadopoulos, MD, Kassiani Theodoraki, MD, Lila Papadimitriou, MD, PhD, and John Papadimitriou, MD, PhD, Anesthetic and Perioperative Management of Adult Transplant Recipients in Nontransplant Surgery, Anesth Analg 1999;89:613-22, 10 pages.
Yungtaek Jang and Milan M. Jovanovic, Constant-Frequency Resonant Inverter for AC-Bus Distribution System, Delta Product Corporation, 2005, 7 pages.
A. Soin, Z. Fang and J. Velasco, Peripheral neuromodulation to treat postamputation pain. In Salvin, K.V. (Ed.), Stimulation of the Peripheral Nervous System: The Neuromodulation Frontier, Progress in Neurological Surgery, 2016; 29:158-167, Chicago, IL: Karger Publishers, 2 pages.
Jiatu Hong, D.M. Vilathgamuwa, N. Ghasemi, T. Ishrat, and Jiang You, A Single Phase DC-AC Dual Active Bridge Series Resonant Converter for Photovoltaic Application, IEEE PEDS 2017, Honolulu, USA, Dec. 12-15, 2017, 6 pages.
Linda Nel and Efrem Eren, Peri-Operative Anaphylaxis. British Journal of Clinical Pharmacology 2011; 71(5):647-658, 12 pages.
Richard P. Williamson and Brian J. Andrews, Localized Electrical Nerve Blocking, IEEE Transactions on Biomedical Engineering, vol. 52, No. 3, Mar. 2005, 9 pages.
Adrien Rapeaux, Emma Brunton, Kianoush Nazarpour and Timothy G. Constandinou, Recovery Dynamics of the High Frequency Alternating Current Nerve Block, first posted online Dec. 15, 2017, 24 pages.
Achir A. Alalami MD, Chakib M. Ayoub and Anis S. Baraka MD, Laryngospasm: review of different prevention and treatment modalities, Pediatric Anesthesia 2008, 18: 281-288, 8 pages.
George Kovacs MD and J. Adam Law MD, Airway Management in Emergencies, Respiratory Care, Feb. 2009, vol. 54, No. 2, 2 pages.
R. Sinclair and M. Luxton, Rapid Sequence Induction. Continuing Education in Anesthesia, Critical Care & Pain, 2005; 5(2):45-48, downloaded from https://academic.oup.com/bjaed/article-abstract/5/2/45/422107 on Jul. 9, 2019, 4 pages.
Meghan G. MacRae, RN, PhD, Closed Claims Studies in Anesthesia: A Literature Review and Implications for Practice, AANA Journal, Aug. 2007, vol. 75, No. 4, 9 pages.

* cited by examiner

DEVICE TO INDUCE ELECTRICAL MUSCLE RELAXATION FOR AIRWAY MANAGEMENT

CROSS-REFERENCE TO RELATED APPLICATION

The present application claims priority to U.S. Provisional Patent Application Ser. No. 62/595,018, filed Dec. 5, 2017, the disclosure of which is expressly incorporated herein by reference.

BACKGROUND AND SUMMARY OF THE DISCLOSURE

Intubation in humans is a known procedure that involves inserting an endotracheal tube into the airway or trachea of a patient in order to maintain an open airway. In emergency cases, once the airway is closed, a common practice is to provide medication treatment to facilitate opening of the airway. Potential drawbacks associated with medication treatment may include delayed onset and offset operation, requirement of intravenous (IV) access, contraindications to use and adverse side effects. These limitations can delay and prevent airway opening and, in some cases, can cause permanent neurologic injury, or death from hypoxia—oxygen deficiency in body tissues. Overcoming these limitations has been a longstanding goal in anesthesiology, and their reduction would decrease morbidity and mortality in both pediatric and adult patients.

The decision to give or not to give a patient muscle relaxant, with potentially serious consequences of either choice, is a dilemma faced routinely in the operating room. The administration of muscle relaxation abolishes a patient's respiratory drive and airway tone. In the majority of circumstances, muscle relaxation will facilitate ventilation and intubation allowing safe management of the airway. Infrequently however, adequate ventilation cannot be achieved and results in a critical "cannot intubate—cannot ventilate" situation. The shortest acting IV muscle relaxants may require 20 minutes for offset. In a "cannot ventilate" situation, waiting 10 minutes for return of spontaneous ventilation will often result in permanent neurologic injury or death in the majority of patients. A recently developed drug, Sugammadex, antagonizes certain muscle relaxants and may shorten this time period to 3 minutes. The airway management system of the present disclosure providing for electrical muscle relaxation could potentially eliminate a "cannot ventilate" scenario, through immediate offset and return to spontaneous ventilation in less than about 1 second.

Succinylcholine is commonly known as the fastest and shortest acting IV muscle relaxant available. Typically, it is the first line agent for situations in which the airway must be secured quickly, such as risk for gastric aspiration. Succinylcholine provides muscle relaxation adequate for intubation in about 90 seconds. The illustrative airway management system of the present disclosure would be superior by providing almost immediate muscle relaxation, reducing the time period in which a patient is at risk for aspiration even further. In trauma situations involving emergency medical technicians (EMTs) and paramedics, emergency departments, and military combat personnel, IV access may not be immediately available. In infants and neonates, IV access may be particularly difficult requiring additional time to establish. The illustrative airway management system of the present disclosure would function independent of IV access, and aid potentially life saving securement of the airway and ventilation in these situations.

Laryngospasm is a reflex closure of muscles in the upper airway resulting in obstructed ventilation. It is most frequently seen in anesthetized children during induction and emergence of anesthesia. The overall incidence of laryngospasm in children 9 years old or younger during anesthesia is 1.74% and in infants between 1 and 3 months, it is 2.82%. If not treated promptly it may result in life threatening consequences such as cardiac arrest, gastric aspiration, pulmonary edema, and arrhythmia. Laryngospasm is successfully treated with muscle relaxation; however, in pediatric anesthesia the majority of patients are induced without IV access. Therefore, treating laryngospasm requires either obtaining IV access prior to administration or giving the medication intramuscularly resulting in delayed onset. Electrical muscle relaxation via the illustrative airway management system of the present disclosure could potentially treat laryngospasm immediately before IV access is obtained, thereby resulting in decreased morbidity.

Contraindications to succinylcholine preclude its use in many high-risk situations. Absolute contraindications to succinylcholine include personal or family history of malignant hyperthermia, muscular dystrophy, neuromuscular disease with denervation, stroke over 72 hours old, burn over 72 hours old, rhabdomyolysis and significant hyperkalemia. Adverse effects of succinylcholine include hyperkalemia, muscle pains, bradycardia, malignant hyperthermia, raised intraocular pressure, raised intracranial pressure, raised intragastric pressure and a high incidence of histamine release and anaphylaxis. The illustrative airway management system of the present disclosure is configured to provide an alternative to succinylcholine in each of the contraindicated scenarios and without its myriad of side effects.

Anaphylaxis is an important source of morbidity and mortality in anesthesia. While likely underreported, the published incidence of perioperative anaphylaxis is between 1 in 6000 to 1 in 20,000 anesthetics. IV muscle relaxants, as a class, have the highest incidence of anaphylactic reactions of all medications given intra-operatively, being responsible for 58.2% of all anesthetic associated anaphylactic reactions. Since electrical induced muscle relaxation does not require the administration of medication, the illustrative airway management system of the present disclosure would remove this serious and potentially fatal risk of anaphylaxis.

It was originally hypothesized that the application of high frequency alternating current (HFAC) caused excessive stimulation of nerves, causing them to become fatigued and thereby resulting in a block. However, later studies contradicted this hypothesis and showed the mechanism to be a direct block of the nerve, likely secondary to tonic depolarization. The difference between a fatigue mechanism and a direct block is important for an illustrative embodiment of the airway management system of the present disclosure, as the former will have a significant recovery time. HFAC block, on the other hand, has a practically instantaneous time to offset of merely 500 ms. Studies have confirmed that HFAC block is effective, repeatable, and quickly reversible.

More recent studies have further characterized HFAC block and its most efficient parameters, opening up the potential for new clinical applications. The most efficient specifications for generating a complete block are a balanced sinusoidal waveform, with a frequency between 5-20 kh. This frequency is an order of magnitude higher than frequencies currently used for electrical muscle stimulation.

HFAC nerve blocks have been studied in animal models, in computer simulation, and more recently in human clinical trials. There is great interest in using HFAC for reduction of chronic pain. As an example, implanted cuffed electrodes with HFAC are currently in clinical trials to block phantom limb pain after amputation. Other current areas of development are relaxing sphincter tone to aid in bladder dysfunction.

An alternative procedure further detailed herein is to cause flaccid paralysis of the muscles of the larynx, neck, jaw, and tongue through electrical stimulation, thereby facilitating airway management. One of the challenges associated with this approach is a non-linear impedance behavior of the skin. Before the conduction path through the skin is established, its impedance is about kilo ohm to several kilo ohms, but once the skin conducts, its impedance drops to hundreds of ohms. Driving nonlinear load such as the body using current source requires a tight control of the current amplitude over a wide load range on the one hand, while on the other hand the appropriate stimulation frequency needs to be maintained to continue the blockade of the nerve. In alternative embodiments, the electrical current can be administered through needle electrodes that penetrate the skin, thus bypassing the high impedance of the skin.

Several stimulation methods and signal patterns are known to influence nerves, and while some implement the power generators, the approaches used are mostly linear, inefficient circuits that are large in size and power hungry. The illustrative airway management system of the present disclosure is configured to implement a portable sinusoidal current generator with a programmable application pattern, with low Total Harmonic Distortion (THD), capable of adjusting and tightly following output frequency and amplitude, creating unique signal patterns suitable to excite the nerves involved.

An illustrative airway management system including an electrical device to produce muscle relaxation for airway management, through a shaped charge that is externally applied, is a novel method that radically would change the current approach to airway management. In contrast to an IV medication, an electrical charge directly and immediately acts on a nerve. It is not affected by circulation time, metabolism or clearance. The system would essentially provide immediate onset and offset operation without IV access and allow use in previously contraindicated conditions.

Recent research has shown that nerves can be completely and consistently blocked, and thereby produce muscle relaxation, through application of a specific high frequency sinusoidal or biphasic charge via an implanted cuffed electrode. For example, electrically blocking the pudendal nerve may aid in restoring urinary voiding. Such invasive practice may be found beneficial for certain applications but lacks practicality in cases of trauma or airway management. The unique concept of the illustrative airway management system of the present disclosure, similar to a Taser stun gun or a defibrillator, employs external electrodes in place of cuffed electrodes. As a result, it non-invasively delivers a shaped charge to the group of nerves that innervate airway muscles, thereby causing muscle relaxation. The charge is delivered in a manner that is safe for both the patient and the operator.

The illustrative airway management system of the present disclosure is configured to 1) externally and non-invasively deliver the specified electrical charge to achieve immediate relaxation of airway muscles; 2) deliver the charge using voltage, current and total charge parameters that are safe for nerves; 3) provide a current path that is safe for the patient as well as the operator; 4) preferentially target airway muscles limiting unintended side effects; 5) provide immediate return of full muscle functionality at offset; and 6) be portable and quickly deployable.

The illustrative system of the present disclosure is applicable to airway management of both adults and children. The illustrative system would be valuable in critical situations in which the airway needed to be secured quickly. In addition, because of the significantly increased margin of safety compared to IV medications, the illustrative system could find use in even routine airway management. The illustrative method of the present disclosure may be used for other important applications in medicine as well. For example, the non-invasive relaxation of smooth muscle could be used to treat status asthmaticus. Additionally, external, non-invasive application of HFAC through our method could be used to treat acute and chronic pain.

According to an illustrative embodiment of the present disclosure, an airway management system to assist in placement of an endotracheal tube within the trachea of a patient, mask ventilation, and/or resolution of laryngospasm, is provided. The airway management system illustratively includes a first electrode configured to be operably coupled to muscle proximate the trachea of the patient, and a power control system operably coupled to a power supply and the first electrode. The power control system is configured to generate an output electrical current pattern to the first electrode, the electrical current pattern including a first current to induce muscle relaxation and a second current to maintain muscle relaxation, the first current being greater than the second current.

According to another illustrative embodiment of the present disclosure, an airway management system includes a first electrode configured to be coupled to skin proximate a trachea of a patient, a second electrode configured to be coupled to the skin proximate the trachea of the patient in spaced relation to the first electrode, and a power control system operably coupled to a power supply, the first electrode and the second electrode. The power control system is configured to generate an output electrical current pattern to the first electrode. The power control system independently regulates an output current frequency and an output current amplitude of the output electrical current pattern.

According to a further illustrative embodiment of the present disclosure, a method of airway management comprises the steps of coupling a first electrode to skin proximate the trachea of a patient, and coupling a power control system to the first electrode and a power supply. The method further includes the step of applying an output electrical current to the first electrode to excite nerves and cause muscle relaxation, thereby opening the trachea.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

A detailed description of the drawings particularly refers to the accompanying figures, in which.

DETAILED DESCRIPTION OF THE DRAWINGS

The embodiments of the invention described herein are not intended to be exhaustive or to limit the invention to the precise form disclosed. Rather, the embodiments selected for description have been chosen to enable one skilled in the art to practice the invention.

Figure 1:
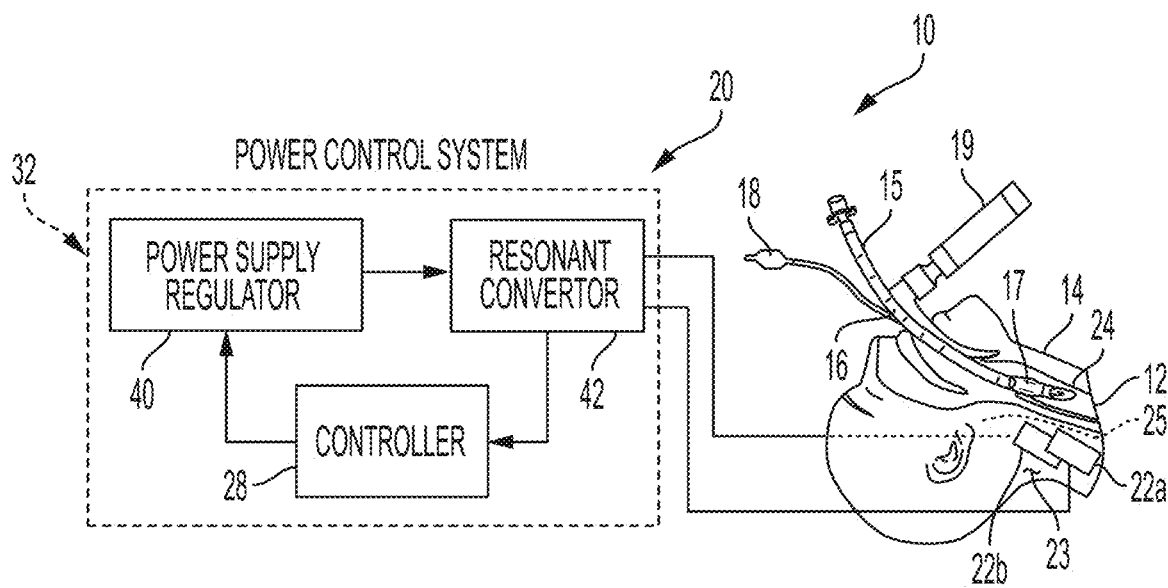
FIG. 1 is a diagrammatic view of the airway management system of the present disclosure coupled to a patient.

Referring initially to FIG. 1, an illustrative airway management system 10 is shown for delivering an electrical current non-invasively to open an airway 12 (e.g., a trachea) of a patient 14. More particularly, the trachea 12 is opened or closed by relaxing and constricting airway muscles 24. As further detailed herein, the opened airway 12 may receive an endotracheal tube (ETT) 15 and/or a laryngoscope 19, and/or facilitate mask ventilation.

Both the endotracheal tube 15 and the laryngoscope 19 may be of conventional design. For example, the endotracheal tube 15 illustratively includes a flexible hollow shaft 16 including a cuff 17 configured to be received within the trachea 12, and a pilot tube 18 extending external of the trachea 12.

The illustrative airway management system 10 includes external electrical contacts or electrodes 22a and 22b configured to deliver electrical current to nerves 25 controlling the patient's airway muscles 24. Illustratively, a shaped electrical charge will cause relaxation of the airway muscles 24 facilitating safe intubation by passage of the endotracheal tube (ETT) 15. Illustratively, the electrodes 22a and 22b are electrically coupled to a power control system 20 including a controller 28. As further detailed herein, the controller 28 is configured to control electrical current supplied to electrodes 22a and 22b via an interface control unit (ICU) 26.

In an illustrative embodiment, the airway management system 10 is configured to deliver high frequency alternating current to nerves 25 via external application of electrodes 22 to essentially block the nerves 25. The electrical current will have to penetrate the skin 23, as well as soft tissue, in order to reach the nerves 25. For example, a higher voltage may be required to penetrate the soft tissues than would be required for an internal cuff electrode, and the tissue may alter the shape of the charge. In certain illustrative embodiments, the electrical current can be administered through needle electrodes 22 that penetrate the skin 23, thus bypassing the high impedance of the skin 23.

In another illustrative embodiment, a different mechanism may be used to cause muscle relaxation of the airway muscles 24. In this case, a stimulating frequency may be applied to the airway muscles 24 (as opposed to a blocking frequency). This stimulation would cause muscle fasciculations, followed by muscle fatigue and relaxation.

In the development of the illustrative airway management system 10, it is necessary to limit potential harm from the system 10 itself. Other electrical medical devices currently in use, and their characteristic charges, suggest that if constructed appropriately, illustrative airway management system 10 will not cause injury. For example, Tasers, defibrillators, and cardioverters use significantly higher voltage than the illustrative airway management system 10.

Figure 2:
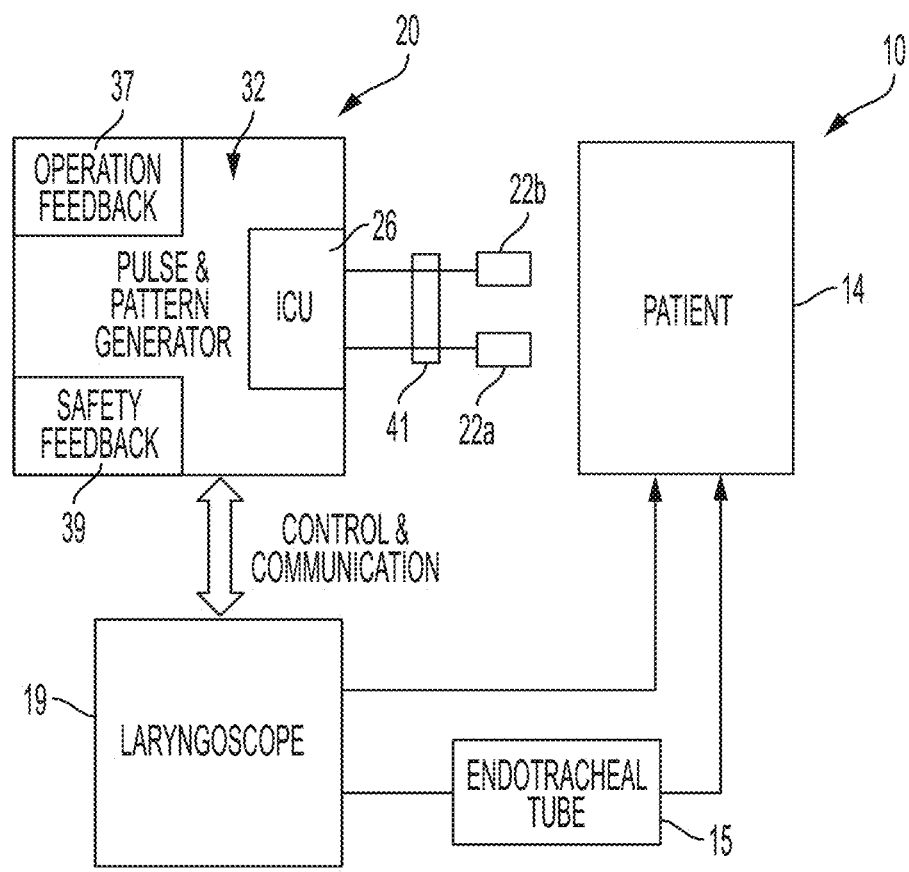
FIG. 2 is a diagrammatic view illustrating interaction between an illustrative power control system including a pulse and pattern generator interacting with a patient.
Figure 3:
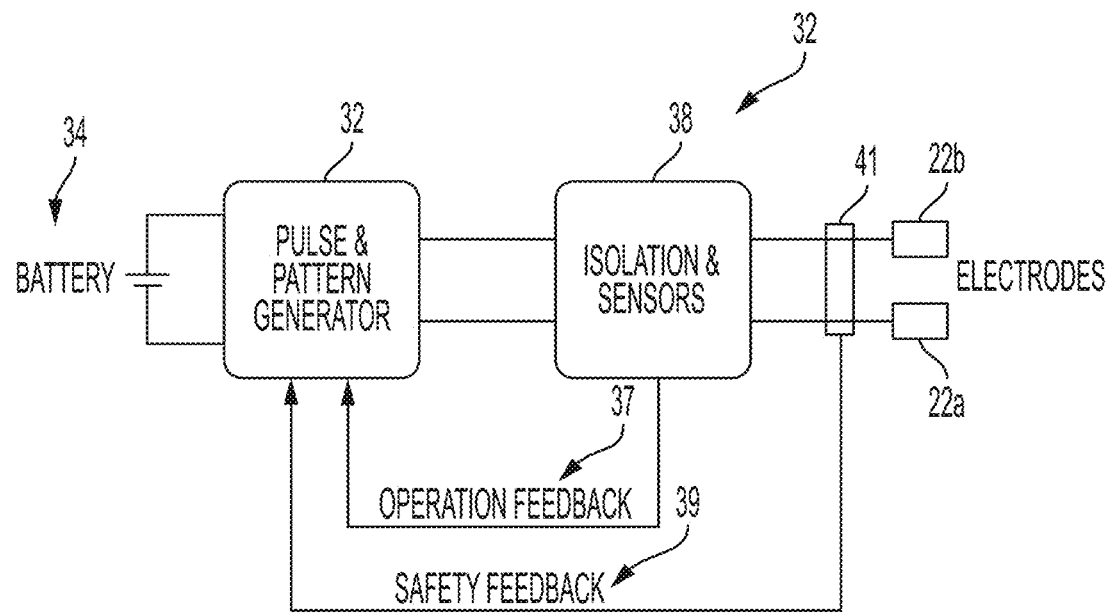
FIG. 3 is a diagrammatic view of an illustrative pulse generator.

With reference to FIGS. 2 and 3, the illustrative airway management system 10 is configured to limit electrical current and charge levels to minimize the risks of electrocution. In order to accurately control this parameter, the airway management system 10 may be built with current source behavior—constant current amplitude with voltage limit. By doing so, the airway management system 10 would build up the voltage to penetrate through the skin 23 (of any moisture level) and other soft tissues, exactly as required without overhead, and at the same time deliver the required electrical current onto the target nerves 25.

With further reference to FIG. 2, the power control system 20 illustratively includes an interface control unit (ICU) 26 operably coupling the electrodes 22 to a pulse and pattern generator 32 coupled to a power source, such as a battery 34 (FIG. 3). As further detailed herein, the pulse and pattern generator 32 (e.g., an electrical drive) is configured to define the amplitude and/or frequency of the electrical current supplied to the electrodes 22.

As shown in FIG. 3, an operation feedback 37 illustratively measures the electrical current delivered to the patient 14 (via sensors 38) and limits the overall electrical current to a safe level (via feedback to the pulse and pattern generator 32). A safety feedback 39 illustratively meters the electrical current flow to/from the electrodes 22 (via contact 41) to limit leakage through other objects (e.g., the operator).

Once muscle relaxation is induced, a much smaller electrical charge may be required to maintain relaxation. The illustrative airway management system 10 may have programmable pattern control. In certain illustrative embodiments, automatic detection may be employed to change the delivery profile of the electrical charge.

The illustrative airway management system 10 is configured with electrodes 22 placed in a way in which the path of the electrical current does not reach the operator or others who may be near or touching the patient 14. Furthermore, since a current sourcing delivery is pursued, it is expected that the synthetic gloves worn by the operator will provide an additional and sufficient isolation layer so that the charge will circulate in its intended path alone. The illustrative airway management system 10 does not require grounding, as the electrical current will circulate between the two electrodes 22a, 22b only without any option to leak to ground and a galvanic isolation transformer may be used.

The illustrative airway management system 10 is configured to use a power supply 34 having a voltage of less than several hundred volts. While this may cause some discomfort in an awake patient 14, a patient 14 undergoing airway management will be anesthetized and completely unconscious. In fact, the stimulation from the illustrative airway management system 10 will likely be significantly less than the directly laryngoscopy and placement of the endotracheal tube 15. Further illustrative airway management systems may be capable of blocking sensory innervation as well as motor innervation. This would result in less stimulation during laryngoscopy than conventional practice.

The placement of electrodes 22 is configured to target specific muscles 24 to limit the overall charge delivered to the patient 14 and unnecessary effects to other regions of the body. The electrodes 22 are illustratively formed of an electrically conductive material and coupled to the skin 23 of the patient 14 via conventional means, such as an adhesive. As further disclosed herein, the electrodes 22 may be needle electrodes that penetrate the skin 23, thus bypassing the high impedance of the skin 23. The electrodes 22 are positioned in proximity to the trachea 12 and the nerves 25 controlling contraction and relaxation of the muscles 24 opening and closing the trachea 12.

It is noted that the vagus nerve is in close proximity to the targeted upper airway muscles 24. The vagus nerve provides parasympathetic innervation to the heart and helps regulate heart rate. It is not expected that the vagus nerve will be affected by the illustrative airway management system 10. However, if the vagus nerve was completely blocked, it would result in a modest increase in heart rate which would not adversely affect the patient. For example, in patients who have received a heart transplant, and thereby had total vagal denervation, loss of vagal influence increases the heart rate to 91-101 beats per minute. The almost immediate onset and offset of the illustrative airway management system 10 provides an additional measure of safety.

The illustrative airway management system 10 is portable and operated by battery 34, thereby allowing for quick deployment in emergency situations, for example, by paramedics or military medical personal. Target specifications and functions outlined above are achievable by means of battery powered supply.

Figure 4A:
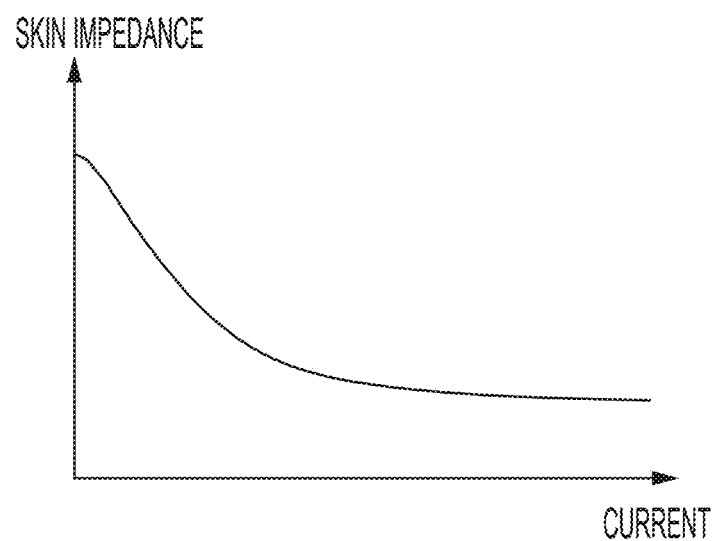
FIG. 4A is a graph showing skin independence behavior.
Figure 4B:
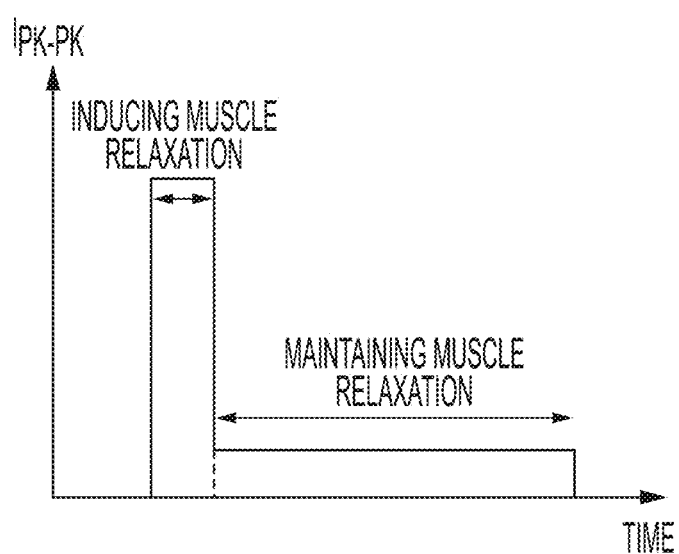
FIG. 4B is a graph showing current pattern generation.
Figure 5:
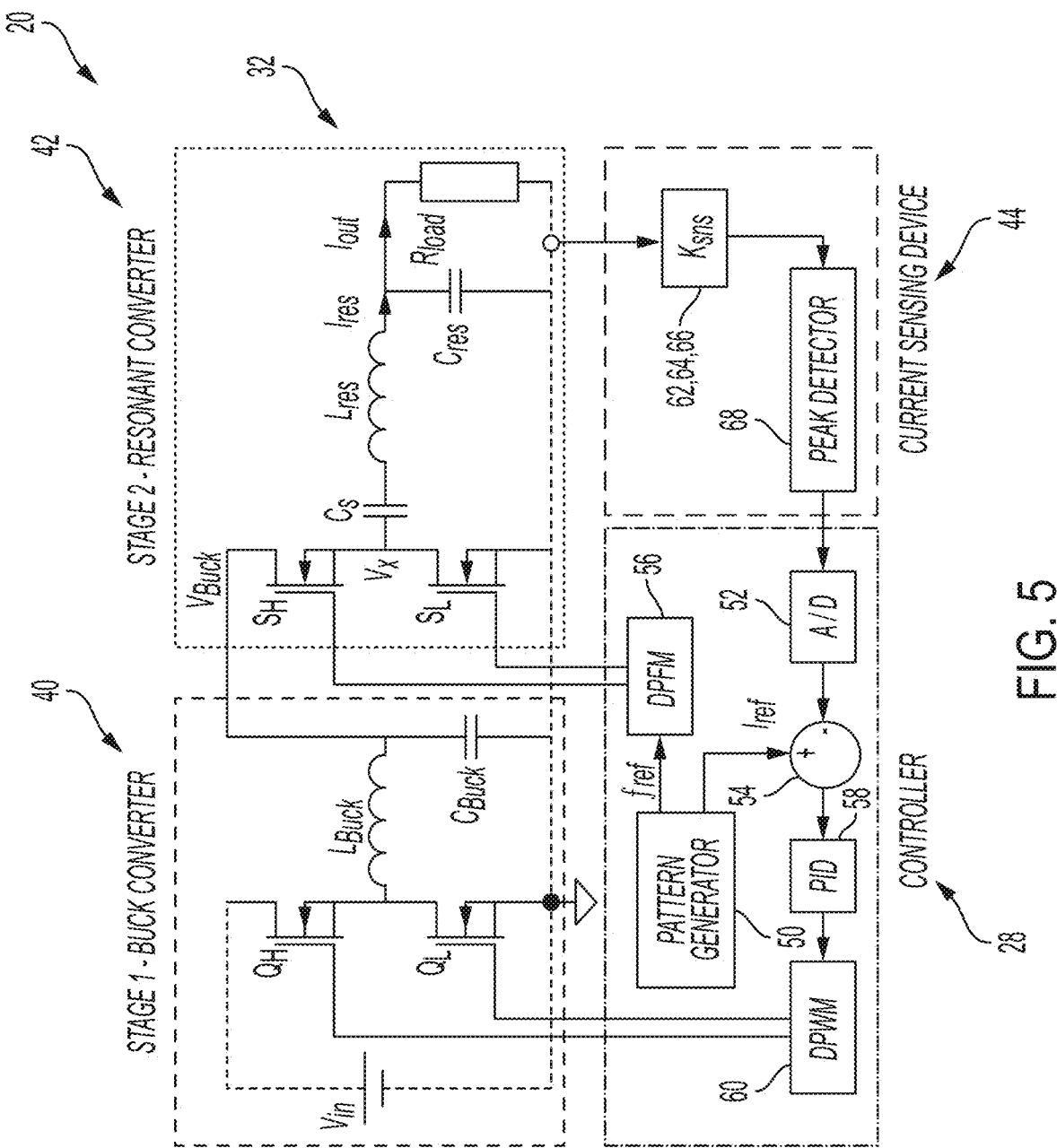
FIG. 5 is a schematic view of the power control system of FIG. 1, including power stage and control blocks.

With reference to FIGS. 4A-5, the illustrative pulse and pattern generator 32 of the airway management system 10 generates sinusoidal current waveforms that can be implemented using a single resonant converter stage. However, when driving a nonlinear load, such as the human body, through the skin and other tissues, there is a challenge to maintain current amplitude as well as programmable frequency. With reference to FIG. 4A, skin impedance behavior is shown as a function of electrical current.

In addition, as shown in FIG. 4B, electrical current requirements to relax the muscle 24 and to maintain it relaxed are shown as not being the same. Higher current is required to initiate muscle relaxation, but once muscle relaxation is induced, a much smaller amplitude current is required in order to maintain relaxation. To address this challenge, a functionality of programmable pattern genera-tion is provided. Additional characteristics of the illustrative airway management system 10 include isolation, which is required to address the safety issue, and total charge regulation to avoid damage to sensitive tissues.

To achieve sinusoidal current waveforms compliant with the goals outlined above, the illustrative pulse and pattern generator 32 implements a two-stage topology. With reference to FIG. 5, the illustrative topology includes a first (e.g., pre-regulation) stage or portion 40 (e.g., a buck converter) followed by a second stage or portion 42 (e.g., a series-resonant parallel-loaded converter). The buck converter 40 adjusts the input voltage to the second stage, whereas the resonant converter 42 produces high frequency alternating current (HFAC). The second stage resonant converter 42 is in charge of generating the sinusoidal waveform at the target frequency with current sourcing attributes, while the first stage buck converter 40 tunes the output current amplitude to meet the reference current and compensates the resonant tank gain variation over the frequency range of interest.

There are several illustrative options for the resonant converter 42 suitable to generate sinusoidal waveforms with low Total Harmonic Distortion (THD). The simplest and easiest for implementation is the series resonant converter. However, for the range of frequencies required to excite the nerve 25, a very high inductance is required to achieve reasonably high quality factor, Q to maintain THD, which in turn translates into a physically large inductor size (See, e.g., equation (1) below). The topology of choice in the illustrative pulse and pattern generator 32 is the series-resonant parallel-loaded converter 42, which has a higher quality factor, $Q_{parallel}$ than the quality factor of the series resonant circuit, $Q_{serial}$ at larger resistances and so it is more suitable for the application.

$$Q_{parallel} = \frac{R_{load}}{Z_r}, \quad Q_{serial} = \frac{Z_r}{R_{load}}, \quad Z_r = \sqrt{\frac{L_{res}}{C_{res}}} \quad (1)$$

The illustrative series-resonant parallel-loaded converter 42 operates by switching the half bridge switches $S_H$, $S_L$ (FIG. 5) in a complementary manner driving the resonant network at the target frequency. When switching frequency $f_{sw}$, is in the vicinity of the resonant frequency $f_{res}$, $f_{res} \approx f_{sw}$, a first harmonic approximation can be applied and the half bridge inverter is described as a sinusoidal source connected to a series resonant network with a parallel load. The voltage $V_x$ can be described as:

$$V_x = \frac{2V_{Buck}}{\pi} \sin(2\pi f_{sw} t) + \frac{V_{Buck}}{2} \quad (2)$$

To avoid DC currents through the inductor, blocking capacitor $C_s$ is used. For $C_s \gg C_{res}$ the expression for output current according to the notations of FIG. 5 is:

$$I_{out} = \frac{2V_{Buck}}{\pi \cdot R_{load}} \cdot \frac{1}{1 + s\frac{L_{res}}{R_{load}} + s^2 L_{res} C_{res}} \quad (3)$$

where the resonant frequency $f_{res}$ is:

$$f_{res} = \frac{1}{2\pi\sqrt{L_{res}C_{res}}} \quad (4)$$

It can be seen from equation (3) that the output current depends on both the input voltage $V_{Buck}$ and the load $R_{load}$. Therefore, in order to maintain constant output current in the presence of load changes and fixed frequency, additional degree of freedom is required, such as the ability to change the input voltage to the resonant stage $V_{Buck}$.

The function of the pre-regulation stage 40 is to adjust the amplitude of the output current in the presence of wide load and input voltage variation. Input voltage variation could be due to charge/discharge of the battery 34, while load variation comes from non-linear characteristics of the skin 23. Pre-regulation stage 40 could be a DC-DC converter to provide step-up, step-down or step-up/down options depending on the source, and desired operation range. Illustratively, a step down buck converter 40 may be operably coupled to a standard laboratory power supply.

The illustrative impact of skin conduction on the converter loading is shown in FIG. 4A. For the matter of response evaluation, skin-loading behavior could be approximately modeled as a step from high impedance to low impedance load. Step from high impedance to low impedance results in a rise of the load current amplitude. One possible option to compensate the change in output current amplitude is to shift the switching frequency and change the gain of the resonant converter 42. This is however, may be prohibitive in the application where both THD and tight frequency control are required. The alternative solution is to use pre-regulation stage to adjust the voltage fed to the resonant converter 42, which in turn adjusts the amplitude of the output current. Pulse Width Modulation (PWM) control is illustratively employed to adjust the output of the buck converter 40, and the control loop is designed to adjust the duty cycle of the buck converter 40 as a function of the amplitude of the sinusoidal output current.

Figure 6A:
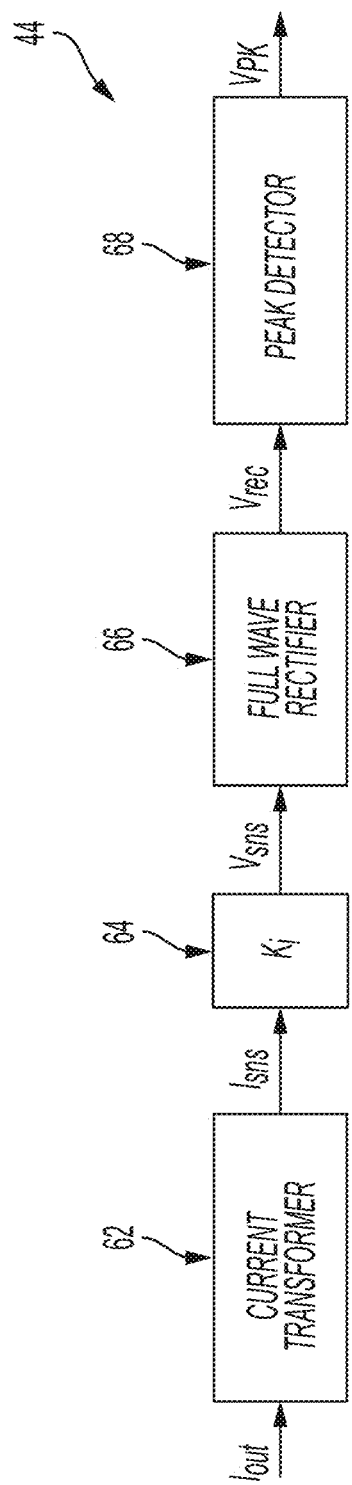
FIG. 6A is a schematic view of an illustrative current sensing device.
Figure 6B:
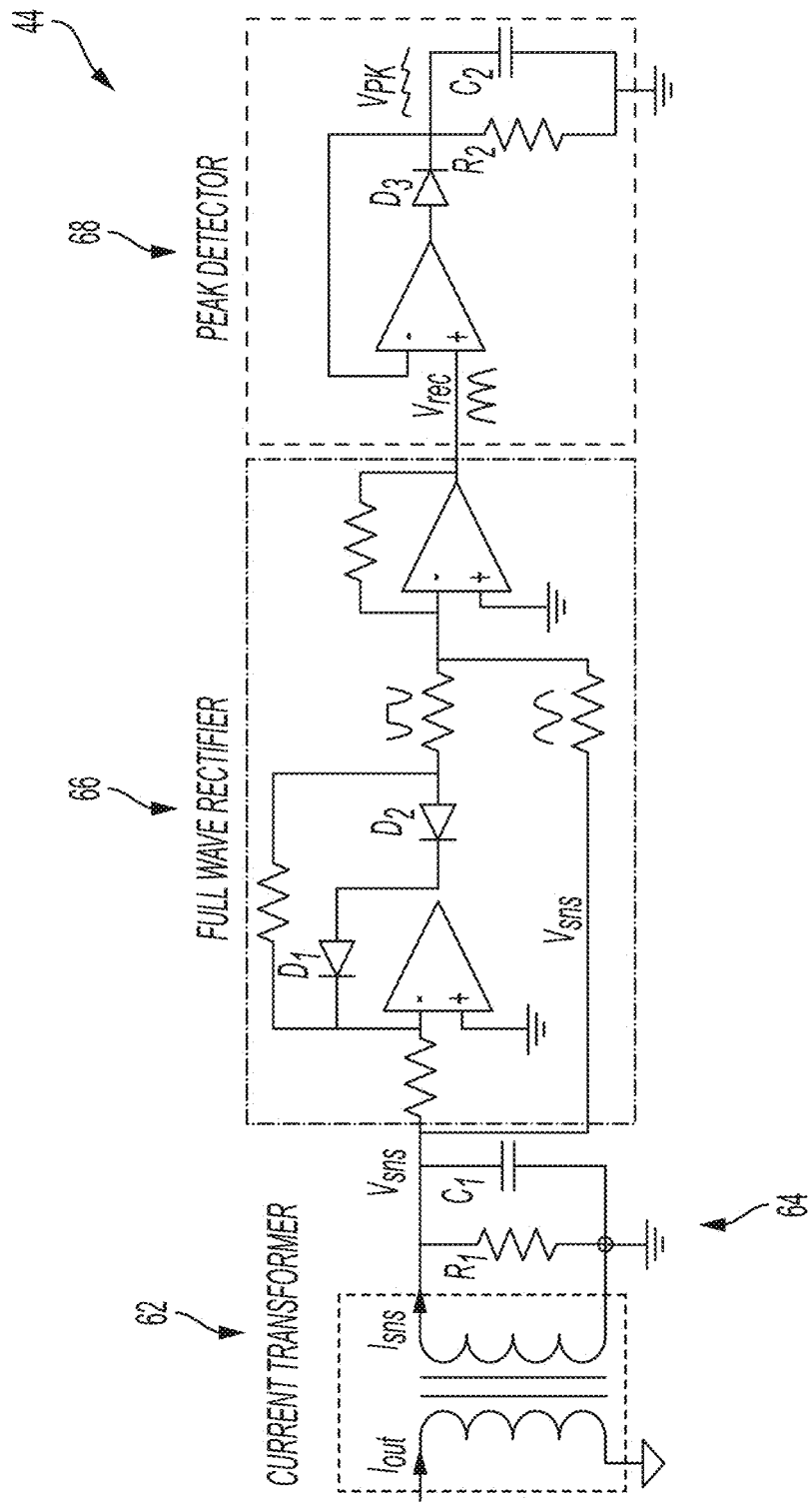
FIG. 6B is a circuit level schematic view of the illustrative current sensing device of FIG. 6A.

A current sensing device 44 is illustratively coupled intermediate the resonant converter 42 and the controller 28. With reference to FIGS. 6A and 6B, an illustrative current sensing device 44 is shown. One of the options to implement current sensing of an AC signal is using a current transformer. The benefit of the method comparing for example to a series-sense resistor, is the efficiency. Current amplitudes required in this study are in the range of 1 mA to 30 mA. In order to facilitate good signal to noise ratio and to create an acceptable interface to an Analog to Digital Converter (ADC) 52 of the controller 28, the sensed current is passed through several gaining and shaping units (FIG. 6A). First is the current transformer 62, which is designed with high transfer ratio, 1:100 in this work. Then the current at the secondary, $I_{sns}$ is converted into voltage by flowing through resistor $R_1$ of RC circuit 64 (FIG. 6B). It should be noted that although low current amplitudes are measured, a high attenuation current sensor is used. This is to facilitate reduced interference measurement with low power consumption. In addition, since the output current (rather than the resonant one) is the target of this application, it is desired to add minimal amount of additional parasitic inductance to the loop. Capacitor $C_1$ of RC circuit 64 is used to smooth the voltage waveform.

With further reference to FIGS. 6A and 6B, a full wave rectifier 66 built around operational amplifier both rectifies the sinusoidal signal and further amplifies it to match the dynamic level of the controller's built in ADC 52. Finally, to reduce the sampling rate requirements of the ADC 52, and reduce its power consumption, an analog peak detector 68 is used. Peak detector 68 is implemented around operational amplifier to allow compensation of the rectifying diode $D_3$ voltage drop. The time constant of the peak detector 68 is selected approximately ten times the period of the sinusoidal waveform to both, filter out the ripple, and smoothly follow the sinus peak value. The amplifiers are fed with bipolar power supply to allow the negative input of the sinusoidal waveform. Alternatively, the potential of full wave rectifier reference and the secondary winding of the current transformer 62 could be raised enough above the ground to allow unidirectional operation.

As noted above, the illustrative power control system 20 is configured to maintain constant output electrical current in the presence of wide non-linear load variation introduced mainly by the human skin 23 (FIG. 4A). More particularly, the illustrative power control system 20 generates an ideal sinusoidal current source. Resonant circuits could be treated as current sources in the immediate vicinity of their resonant frequency. However, it is unpractical in the real system 10 due to very high quality factor required, which in turn poses another challenge of locking in the operation frequency close enough to the resonant frequency. Finally, if the operation frequency needs to be adjusted on demand, to maintain current source characteristics a continuously variable resonance component is required. An alternative to ideal current source would be a controlled system 10 that is able to regulate the frequency and the output current amplitude independently. The user has an independent freedom to change the frequency of the second stage, by adjusting the switching frequency of the resonant converter 42, and to adjust the output current amplitude by regulating the voltage of the first stage defined by the buck converter 40 (FIG. 5).

Figure 7:
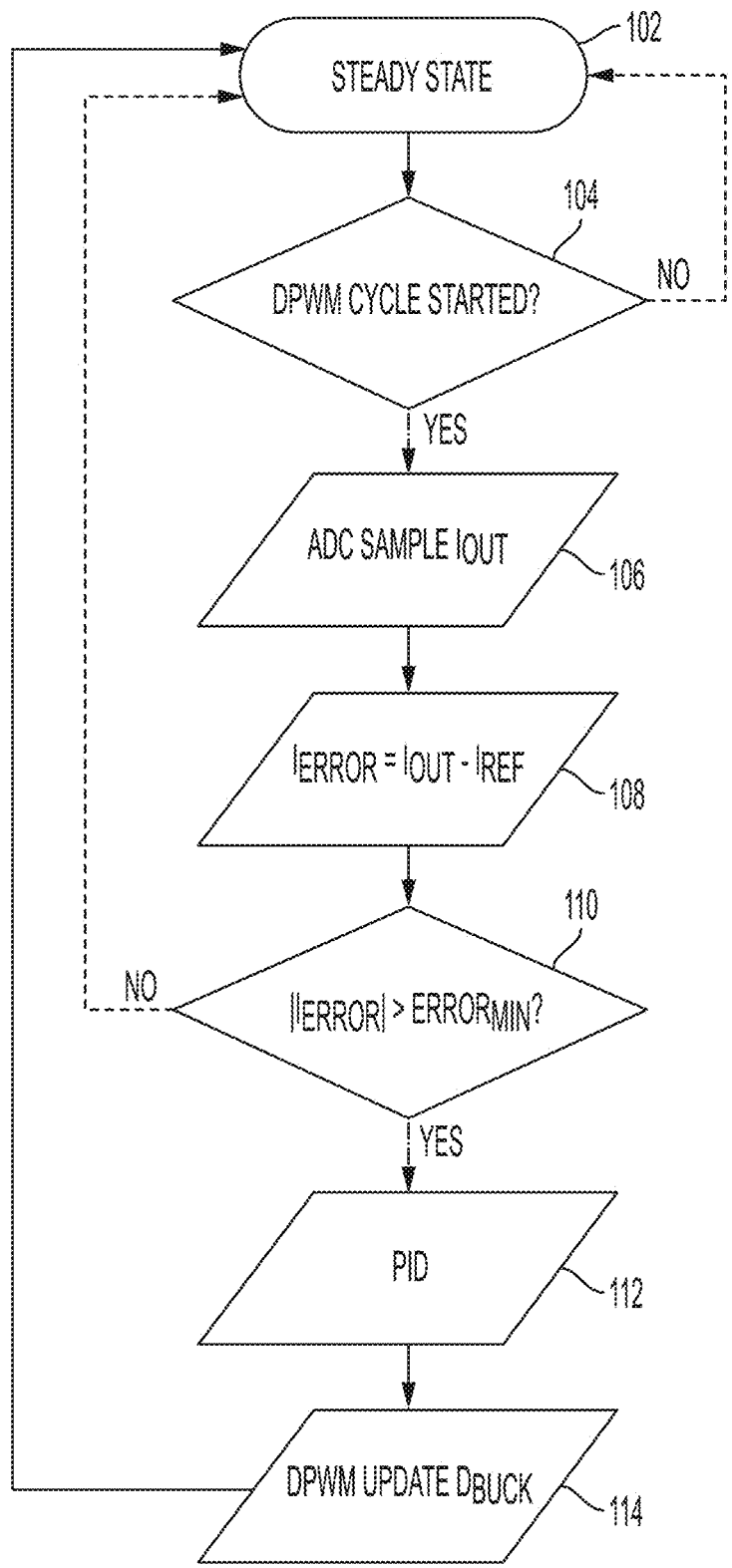
FIG. 7 is a flow chart showing illustrative operation of the two-stage controller of FIG. 5.

A flowchart of the illustrative method of operation of the power control system 20 is shown in FIG. 7. More particularly, functional blocks 102-114 demonstrate operation of an illustrative algorithm by the controller 28. To address the control management requirements, the controller 28 is illustratively defined by a microcontroller (MCU). With further reference to FIGS. 5 and 7, the process illustratively starts at steady state block 102. During every cycle of the resonant stage (block 104), the output voltage of the peak detector 68 $V_{PK}$ is sampled by an AC to DC converter (ADC) 52 (block 106). Then, a calculation of the current error is performed by comparator 54 at block 108. At block 110, if the error exceeds a maximum acceptable limit, a proportional-integral-derivative (PID) compensator 58 calculates the new duty cycle $D_{Buck}$ at block 112. The new duty cycle $D_{Buck}$ is then fed to the front-end stage or buck converter 40 via a digital pulse width modulator (DPWM) 60 at block 114.

An additional MCU function is pattern generation. The references of frequency and amplitude provided to the controller 28 by the pattern generator 50 (FIG. 5) are varied in time to achieve certain medical functionality. The pattern generator 50 is operably coupled to a digital pulse frequency modulator (DPFM) 56. In the example shown in FIG. 4B, first muscle relaxation is induced with a first higher current for short period, and then in order to hold the muscle relaxed, the current is significantly reduced to a second current and maintained for a longer period.

An important aspect of medical devices relates to safety concerns for both the subject (e.g., patient 14) and the user (e.g., caregiver). To assure that electrical current flows on to the subject alone within the confined region of the contact electrodes 22, i.e., there is no electrocution hazard to the applicator, the current flow is governed and monitored on both electrodes 22. This can be facilitated using a single current transformer 62, occupying two turns on its primary, one turn from the signal line and the other from the return path. A zero-sum reading of the transformer 62 assures that the entire current flows in the desired path without leakage. It should be noted that although isolation is used in the application, parasitic capacitance leakage is still feasible, and therefore an extra measure of caution has been employed. To satisfy the safety of the patient 14, and to prevent damage or burn of the sensitive tissues due to arching, the charge flow out of each electrode 22 is continuously monitored, so that the application does not exceed the allowed per pulse as well as accumulative charge quantity.

The load range of the converter 42 is located in between 100Ω to 1 kΩ. The minimum quality factor, $Q_{min}$ of the series-resonant parallel-loaded converter 42 is selected according to the THD requirements. Very high quality factors however, are undesired. High quality factor results in much higher reactive currents that circulate in the system and reducing system efficiency, steep transfer function that is challenging in terms of frequency and gain control. In addition, an underdamped system has long convergence time. Therefore, the upper limit for the quality factor is limited to around 100, while the minimum quality factor has been selected to be three. To maintain the minimum quality factor, the design of the converter 42 is carried out for the worst-case conditions, i.e. the load resistance of 100Ω.

Operation of the converter 42 is desirable in the inductive range, i.e. above the resonance frequency of the RLC network, which provides current sourcing behavior and enables ZVS of the main resonant converter 42 switches, and as a result, lower losses are obtained. The target operation-frequency range in this study is set to 10 kHz-40 kHz, which is the most prominent range for nerve manipulation according to the medical studies. The resonant frequency of the series resonant tank is selected slightly lower than the lowest expected operation frequency. Using equations (1), (4) and the considerations of the resonant frequency and quality factor outlined above the product of $L_{res}$ and $C_{res}$ is set to:

$$C_{res} = \frac{Q_{min}}{2\pi f_{res} R_{min}}, L_{res} = \frac{1}{C_{res}(2\pi f_{res})^2} \quad (5)$$

where $Q_{min}$ is the minimum quality factor, $R_{min}$ is the minimum output load.

To avoid DC offsets associated with parallel loading of the series resonant circuit fed off a half bridge, a blocking capacitor $C_s$ is used. Blocking capacitor $C_s$, is selected to be large enough comparing to the resonant capacitor $C_{res}$, to minimize the ripple and maintain the voltage constant. Resonant inductor is designed for the worst-case conditions as well, which is the highest expected current in the circuit. The inductor in this circuit configuration carries larger current than the current provided to the load. The ratio between the output current $I_{out}$ and resonant inductor current $I_{res}$ could be summarized in the following expression:

$$I_{res} = I_{out} \cdot \sqrt{1 + \left(\frac{f_{min}}{f_{res}} \cdot Q\right)^2} \quad (6)$$

Therefore, the worst-case conditions for resonant inductor occur at the maximum load resistance, highest quality factor, and minimum allowed switching frequency $f_{min}$. The lowest switching frequency $f_{min}$ is the converter operation frequency closest to the resonant frequency, $f_{res}$.

To validate the design presented in this study a laboratory prototype of the illustrative power control system 20 including a two stage resonant sinusoidal generator has been designed and built. The converter 42 is digitally controlled by a dsPIC33FJ16GS502 microcontroller 28 manufactured by Microchip Technology Inc. of Chandler, Ariz., USA. Illustrative parameters of the power control system 20 are summarized in Table I below:

TABLE I

| TWO STAGE SYSTEM PARAMETERS | |
|---|---|
| Component | Value/Type |
| Input voltage $V_{in}$ | 20 V |
| $R_{load}$ range | 100-1000 Ω |
| Output voltage $V_{out}$ | 10 V-50 V pk-pk |
| Frequency range $f_{ref}$ | 10 kHz-40 kHz |
| Resonant capacitor $C_{res}$ | 150 nF |
| Resonant inductor $L_{res}$ | 2 mH |
| Blocking capacitor $C_s$ | 1.1 µF |

Figures 8A, 8B:
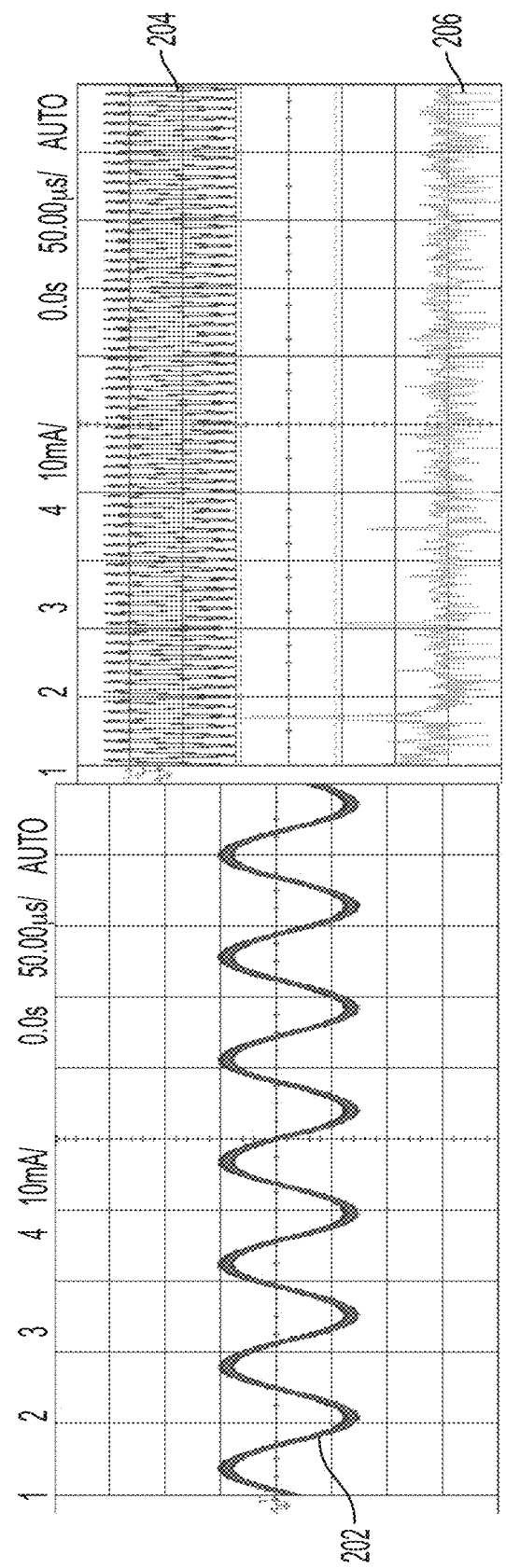
FIG. 8A is a graph showing illustrative converter operation in the form of time domain sinusoidal output current, Iout (10 mA/div), and horizontal axis (50 us/div)
FIG. 8B is a graph showing illustrative converter operation in the form of fast Fourier transform (FFT) of the output current, with the top trace representing output current Iout (10 mA/div), and horizontal axis (500 us/div), and with the bottom trace representing FFT of the output current (20 dB/div), and horizontal axis (20 kHz/div)

Illustrative operation of converter 42 is shown in FIG. 8. Illustrative time domain sinusoidal output current waveform $I_{out}$ (10 mA/div) 202 with low distortion is shown in FIG. 8A, where the horizontal axis reference is 50 µs/div. The FFT transformation of $I_{out}$ is shown in FIG. 8B. The upper trace 204 represents output current $I_{out}$ (10 mA/div) with a horizontal axis reference of 500 µs/div, while the lower trace 206 represents FFT of the output current (20 dB/div) with a horizontal axis reference of 20 kHz/div. The THD of the waveform in FIG. 8B has been calculated based on the FFT values, and found to be 2%.

Figures 9A, 9B:
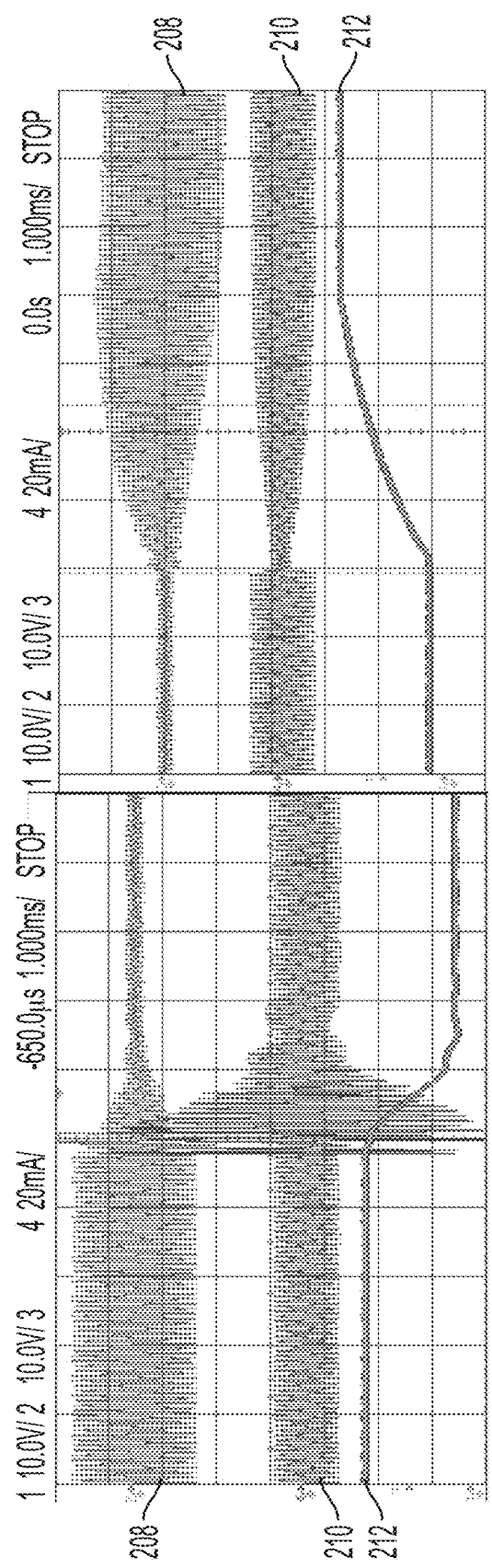
FIG. 9A is a graph showing illustrative load change compensation, 1000[Ω] to 100[Ω], with the top trace representing output voltage $V_{out}$ (10V/div), the middle trace representing output current $I_{out}$ (20 mA/div), and the bottom trace representing input voltage of the second stage $V_{Buck}$ (10V/div)
FIG. 9B is a graph showing illustrative load change compensation, 100[Ω] to 1000[Ω], with the top trace representing output voltage $V_{out}$ (10V/div), the middle trace representing output current $I_{out}$ (20 mA/div), and the bottom trace representing input voltage of the second stage $V_{Buck}$ (10V/div)

Illustrative response of the power control system 20 to load changes is demonstrated in FIG. 9. The top traces 208 represent the output voltage $V_{out}$ (10V/div). The middle traces 210 represents the output current $I_{out}$ (20 mA/div). The bottom traces 212 represent the input voltage of the second stage $V_{Buck}$ (10V/div). A step from light load 1 kΩ to heavy load 100Ω, i.e. the condition of high initial resistance of the skin 23 that is reduced after the conduction is initiated, is shown in FIG. 9A. The system adjusts to the reference output current in less than 2 ms, which is approximately 30 switching cycles of 14 kHz sinusoidal waveform, and is approximately the quality factor of the circuit at these conditions. An opposite step from heavy load of 100Ω to the light load of 1 kΩ is shown in FIG. 9B.

Figures 10A, 10B:
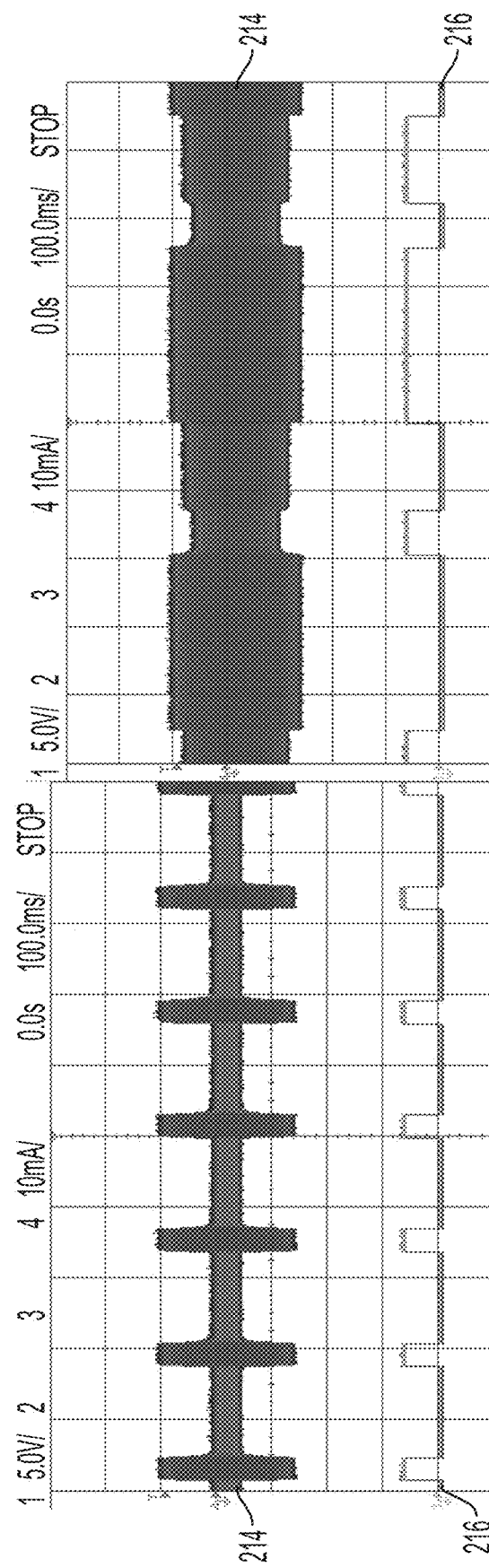
FIGS. 10A and 10B are graphs showing illustrative pattern generation with changing current amplitude, with the top trace representing output current Iout (10 mA/div), and the bottom trace representing the pattern synchronization signal.

Illustrative current pattern generation capability is shown in FIG. 10. Top traces 214 represents output current $I_{out}$ (10 mA/div), while bottom traces 216 represents pattern synchronization signal. Current pattern that was discussed in FIG. 4A that requires higher current for short period to induce muscle relaxation, and then much lower current to maintain muscle relaxation is shown in FIG. 10A, repeated at 6 Hz. An additional current pattern with three different amplitudes and time periods is shown in FIG. 10B.

As further detailed herein, the illustrative airway management system 10 includes a two stage sinusoidal current generator 32 for muscle manipulation over the skin 23. High THD along with independent frequency and amplitude generation is achieved. The generator 32 is configured to generate continuous current patterns tightly following the reference values in the presence of a non-linear load, the patient's skin 23 in this case.

Although the invention has been described in detail with reference to certain preferred embodiments, variations and modifications exist within the spirit and scope of the invention as described and defined in the following claims.

The invention claimed is:

1. An airway management system for use with a patient, the airway management system comprising:
   a first electrode configured to be operably coupled to muscle proximate the trachea of a patient; and
   a power control system operably coupled to a power supply and the first electrode, the power control system including a two stage sinusoidal current generator configured to generate an output electrical current pattern to the first electrode, the current generator including a first stage and a second stage, the first stage configured to adjust an output current amplitude provided to the second stage, the second stage generating the output electrical current pattern with a sinusoidal waveform at a target frequency, the electrical current pattern including a first current to induce muscle relaxation and a second current to maintain muscle relaxation, the first current being greater than the second current.

2. The airway management system of claim 1, wherein the second stage of the power control system includes a resonant converter operably coupled to the first electrode.

3. The airway management system of claim 2, wherein the first stage of the power control system further includes a power supply regulator operably coupled to the resonant converter for regulating the output current amplitude.

4. The airway management system of claim 3, wherein the power control system further includes a buck converter operably coupled to the resonant converter.

5. The airway management system of claim 3, wherein the power control system further includes a controller operably coupled to the power supply regulator, and a current sensing device operably coupled to the resonant converter and the controller.

6. The airway management system of claim 1, further comprising an endotracheal tube for positioning within the trachea of the patient.

7. The airway management system of claim 1, further comprising a second electrode operably coupled to the power control system and configured to be coupled to skin proximate the trachea of the patient in spaced relation to the first electrode.

8. A method of airway management comprising the steps of:
   coupling a first electrode to skin external to airway muscles and proximate the trachea of a patient;
   coupling a power control system to the first electrode and a power supply;
     applying an output electrical current to the first electrode to excite nerves and cause muscle relaxation, thereby opening the trachea; and
     independently regulating an output current frequency and an output current amplitude of the output electrical current.

9. The method of claim 8, further comprising the step of inserting an endotracheal tube within the trachea of the patient.

10. The method of claim 8, further comprising the step of coupling a second electrode to the skin proximate the trachea of the patient in spaced relation to the first electrode.

11. The method of claim 8, wherein the step of independent regulating includes generating sinusoidal current waveforms to the first electrode.

12. The method of claim 11, wherein the step of independent regulating includes generating a first current to induce muscle relaxation and a second current to maintain muscle relaxation, the first current being greater than the second current.

* * * * *